(12) United States Patent
Zanella (10) Patent No.: US 8,029,478 B2
(45) Date of Patent: Oct. 4, 2011

(54) IMPLANTABLE DEVICE AND METHOD FOR DELIVERING DRUG DEPOTS TO A SITE BENEATH THE SKIN

(75) Inventor: John Zanella, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 397 days.

(21) Appl. No.: 11/932,442

(22) Filed: Oct. 31, 2007

(65) Prior Publication Data

US 2009/0112177 A1    Apr. 30, 2009

(51) Int. Cl.
*A61B 17/56* (2006.01)
*A61B 17/04* (2006.01)
*A61M 31/00* (2006.01)
*A61M 5/32* (2006.01)

(52) U.S. Cl. ........ 604/175; 604/93.01; 606/53; 606/300

(58) Field of Classification Search .......... 604/158–163; 424/423
See application file for complete search history.

(56) References Cited

U.S. PATENT DOCUMENTS

| | | | |
|---|---|---|---|
| 4,781,695 A * | 11/1988 | Dalton | 604/175 |
| 5,207,678 A | 5/1993 | Harms et al. | |
| 6,086,614 A | 7/2000 | Mumme | |
| 6,936,270 B2 * | 8/2005 | Watson et al. | 424/423 |
| 7,012,106 B2 | 3/2006 | Yuan et al. | |
| 2002/0198527 A1 | 12/2002 | Muckter | |
| 2004/0220547 A1 | 11/2004 | Heruth | |
| 2006/0100622 A1 * | 5/2006 | Jackson | 606/61 |
| 2006/0253100 A1 | 11/2006 | Burright | |
| 2007/0123863 A1 * | 5/2007 | Winslow et al. | 606/61 |
| 2009/0088809 A1 * | 4/2009 | Fisher et al. | 606/302 |

FOREIGN PATENT DOCUMENTS

WO    9320859    10/1993

OTHER PUBLICATIONS

U.S. Appl. No. 11/403,733, filed.

* cited by examiner

*Primary Examiner* — Theodore Stigell
*Assistant Examiner* — Imani Hayman (57) ABSTRACT

An implantable device and method is provided for anchoring a drug depot to a site beneath the skin of a patient, the device and method comprising a head, a shaft and a tip, the head having a recess and/or at least one projection arranged to be engaged by an implantation tool, the shaft having an outer surface that engages the site in a manner that holds the device at the site beneath the skin, the head or shaft having members for attaching the drug depot thereto, and the tip disposed on the shaft opposite the head and capable of insertion into the site beneath the skin of the patient.

16 Claims, 5 Drawing Sheets

IMPLANTABLE DEVICE AND METHOD FOR DELIVERING DRUG DEPOTS TO A SITE BENEATH THE SKIN

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Sometimes, after the drug depot is implanted at the treatment site, the drug depot may migrate from the implant site as physiological conditions change (e.g., repair and regeneration of cells, tissue ingrowth, movement at implant site, etc.). At times, this may reduce efficacy of the drug as the drug depot migrates away from the implant site and lodges in a distant site. If this occurs, the drug depot will have to be removed from the distant site and have to be reinserted causing additional physical and psychological trauma to a patient. In some cases, if the drug depot migrates into a joint, the drug depot may inhibit movement. In more severe cases, if the drug depot migrates, it may restrict blood flow causing an ischemic event (e.g., embolism, necrosis, infarction, etc.), which could be detrimental to the patient.

Previously, implantable devices have been used to stabilize tissue (e.g., bone, joints, etc.) or used to bridge gaps between ruptured tissues. These implantable devices include rigid anchoring members, which allow little or no movement at the implant site; flexible anchoring members that stabilize the joint and allow some degree of movement; retaining anchoring members that are bolted to one side of a joint and engage like a hook on the opposite side; and anchoring members with articular connections to bridge gaps and stabilize tissue.

New implantable devices are needed that improve the drug depot efficacy and reduce the risk associated with unwanted migration of the drug depot. Implantable devices that allow accurate and precise implantation of the drug depot with minimal physical and psychological trauma to the patient are also needed.

SUMMARY

New implantable devices that improve drug depot efficacy and reduce unwanted migration of the drug depot are provided. One advantage of the implantable device is that it allows, in various embodiments, accurate and precise implantation of a drug depot with minimal physical and psychological trauma to the patient. Another advantage of the implantable device is that it allows easier replacement of an exhausted drug depot with a fresh new drug depot.

In one exemplary embodiment, an implantable device is provided for anchoring a drug depot adjacent to a site beneath the skin of a patient, the device comprising: a head, a shaft and a tip, the head having a recess and/or at least one projection arranged to be engaged by an implantation tool, the shaft having an outer surface that engages the site in a manner that holds the device at the site beneath the skin, the head or shaft having means for attaching the drug depot thereto, and the tip disposed on the shaft opposite the head and capable of insertion into the site beneath the skin of the patient.

In another exemplary embodiment, an implantable device is provided for anchoring a drug depot to a site beneath the skin of a patient, the device comprising: a head, a shaft and a tip, the head having a recess and/or at least one projection arranged to be engaged by a turning tool and for attaching the drug depot thereto, the shaft having a threaded outer surface that engages the site in a manner that holds the device at the site beneath the skin, and the tip being located on the shaft opposite the head and capable of insertion into the site beneath the skin of the patient.

In yet another exemplary embodiment, a method is provided for delivering a drug depot adjacent to a site beneath the skin of a patient, the method comprising: implanting a device comprising a head, a shaft and a tip, the head having a recess and/or at least one projection capable of being engaged by a turning tool and means for attaching the drug depot thereto, the shaft having a threaded outer surface that engages the site in a manner that holds the device at the site beneath the skin, and the tip being located on the shaft opposite the head and being capable of insertion to the site beneath the skin of the patient; engaging the recess and/or the projection of the head with the turning tool and turning the head causing the tip to be inserted into the site in such a manner so as to cause the outer surface of the shaft to engage the site; and attaching the drug depot to the recess and/or the projection of the head of the device, thereby anchoring the drug depot adjacent to the site beneath the skin of the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New implantable devices that improve drug depot efficacy and reduce unwanted migration of the drug depot are provided. One advantage of the implantable device is that it allows, in various embodiments, accurate and precise implantation of a drug depot with minimal physical and psychological trauma to the patient. Another advantage of the implantable device is that it allows easier replacement of an exhausted drug depot with a fresh new drug depot.

In one exemplary embodiment, an implantable device is provided for anchoring a drug depot adjacent to a site beneath the skin of a patient, the device comprising: a head, a shaft and a tip, the head having a recess and/or at least one projection arranged to be engaged by an implantation tool, the shaft having an outer surface that engages the site in a manner that holds the device at the site beneath the skin, the head or shaft having means for attaching the drug depot thereto, and the tip disposed on the shaft opposite the head and capable of insertion into the site beneath the skin of the patient.

Implantable Device

Figure 1:
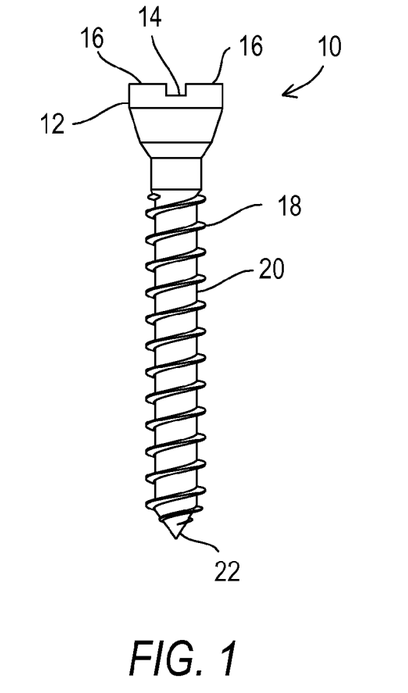
FIG. 1 illustrates an enlarged side view of an embodiment of the implantable device for anchoring a drug depot. In this illustrated embodiment, the implantable device comprises a screw for anchoring the drug depot. The screw having a recess and a plurality of projections arranged to be engaged by an implanting tool.

Referring to FIG. 1, a side view of an embodiment of the implantable device for anchoring a drug depot is illustrated. In this illustrated embodiment, the implantable device 10 comprises head 12, a shaft 20 and a tip 22, the head having a recess 14 and projections 16 arranged to be engaged by an implantation tool and means for attaching the drug depot to the device (not shown). The shaft 20 has a threaded outer surface 18 that engages the implant site in a manner that holds the device at the site beneath the skin. The tip 22 of the implantable device is opposite the head 12 and is capable of insertion into the site beneath the skin of the patient.

The implantable device may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

In various embodiments, some or all of the implantable device and/or the drug depot may comprise material that is biodegradable. Examples of suitable biodegradable material include, but is not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof. In various embodiments, the drug depot degrades before the implantable device. In alternative embodiments, neither the implantable drug depot device nor the drug depot degrade.

The dimensions of the implantable device, among other things, will depend on the site for implantation. The implantable device can be adapted to any size and shape. For example, the width of the epidural space is only about 3-5 mm for the thoracic region and about 5-7 mm for the lumbar region. Thus, the device, in various embodiments, can be designed for these specific areas. Some examples of the size of the device include a width from about 1 mm to about 6 mm and a length from about 5 mm to about 20 mm. In various embodiments, the device will be larger, the same size or smaller than the drug depot.

The tip 22 of the device is designed to penetrate the site specific tissue and cause minimal physical and psychological trauma to the patient. The tip of the implant device may be designed for placement and location within or near the muscle, ligament, tendon, cartilage, bone, synovial joint, spinal disc space, spinal canal or the surrounding soft tissue.

In various embodiments, the device may be implanted in an intra-articular region of a synovial joint where there is no interfacing articular cartilage. It may be located, for example, within the inside of the knee capsule that is non-load-bearing and removed from the articulation surface of the synovial joint. The device may be attached within the synovial joint, allowing for continuous exposure to synovial fluid flow and resulting release of the drug from the drug depot, without damaging the articular surface that is in apposition during range of motion of the given joint.

Once the tip 22 is inserted at or near the site, the shaft 20 holds the device at or near the implant site. Various means can hold or retain the device at or near the site including, but not limited to, threading, tracks, clips, ribs, projections, and the like. Shown in FIG. 1 is a threaded outer surface 18 that holds or retains the device at or near the implant site.

Figure 2:
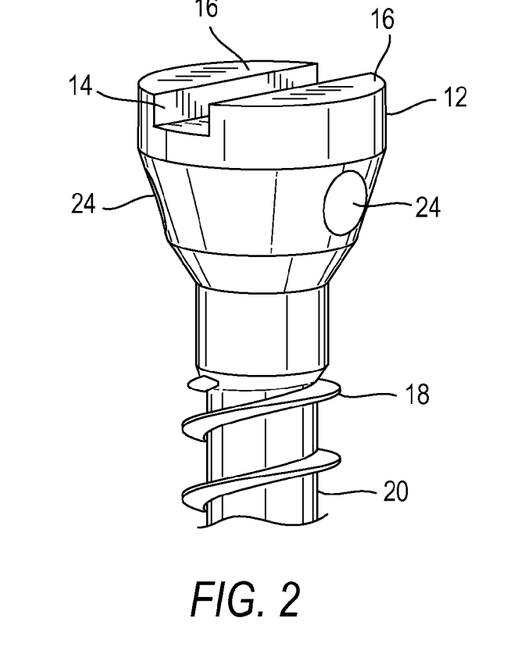
FIG. 2 illustrates an enlarged side view of an embodiment of the head of the implantable device for anchoring a drug depot. In this illustrated embodiment, the implantable device comprises a screw head having a recess, a plurality of projections arranged to be engaged by an implanting tool, and through-holes for attaching the drug depot.

Referring to FIG. 2, an expanded angled side view of an embodiment of the head of the implantable device for anchoring the drug depot is illustrated. In this illustrated embodiment, the implantable device comprises a screw head having a recess 14 and a plurality of projections 16 arranged to be engaged by an implanting tool (not shown) and means for attaching the drug depot to the implantable device. Various means are capable of attaching the drug depot to the implantable device including, but not limited to, holes, eyelets, hooks, and mating pairs that allow the drug depot to be attached to the implantable device (e.g., snap fit members, recesses, projections, wings, internal and external threading, tracks, clips, cleats, and the like). For example, the drug depot comprises a projection that fits into the recess of the implantable device and "snaps into it". In the embodiment illustrated in FIG. 2, the means for attaching the drug depot comprises through-holes 24 radially disposed through the head of the device below the recess and/or projection and aligned so that there is a channel between them that is capable of receiving the drug depot or suitable for attaching the drug depot. In various embodiments, the drug depot may be attached to the implantable device by threading a suture or wire having a drug depot disposed on it through the hole and tying it to the implantable device.

Figure 3:
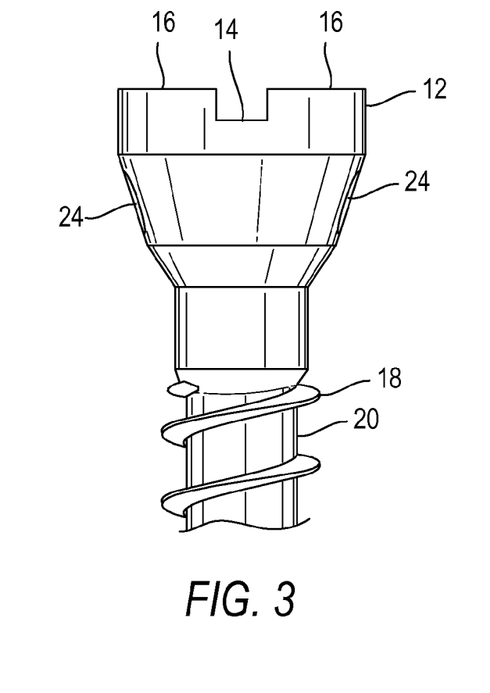
FIG. 3 illustrates an expanded side view of an embodiment of the head of the implantable device for anchoring a drug depot. In this illustrated embodiment, the implantable device comprises a screw head having a recess, a plurality of projections arranged to be engaged by an implanting tool, and through-holes for attaching the drug depot.

FIG. 3 illustrates an expanded side view of an embodiment of the head of the implantable device for anchoring a drug depot. In this illustrated embodiment, the implantable device comprises a screw head 12 having a recess 14 and a plurality of projections 16 arranged to be engaged by an implanting tool (not shown) and through-holes 24 for attaching the drug depot. The projections may be any size and shape (e.g., straight, flat-sided shape, an elliptical shape, bi-concave shape, square shape, or any other protruding shape which provides sufficient implantation tool-engaging end strength and drive purchase to allow transmission of insertional torque without breaking or otherwise damaging the device.

Implantation Tool

Figure 4:
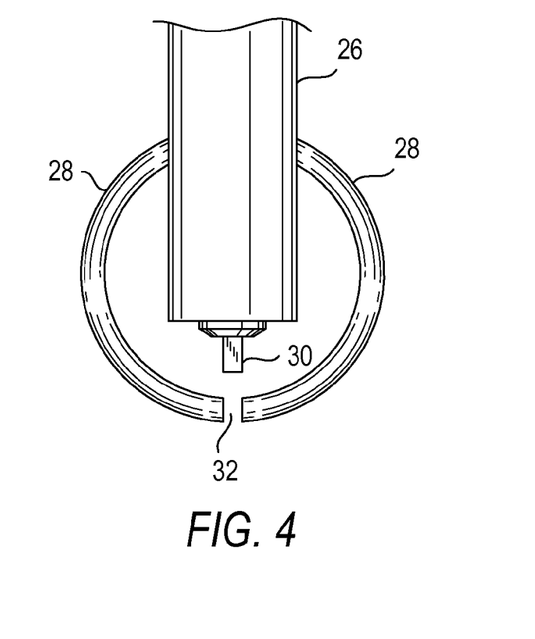
FIG. 4 illustrates an enlarged side view of an embodiment of the implanting tool suitable for engaging the head of the implantable device. The implanting tool having arms for engaging, among other things, the through-holes of the head of the implantable drug delivery device. In this illustration, the implantation tool is in a disengaged position from the device.

FIG. 4 illustrates a side view of an embodiment of the implantation tool suitable for engaging the head of the implantable device. The implanting tool having a body 26 for the user to hold, arms 28 and edge 30 for engaging the through-holes and recess of the head of the implantable drug delivery device. In this illustrated embodiment, the implantation tool is in a disengaged position (e.g., not engaging the implantable device). There is a gap 32 between the arms, and the arms are of sufficient elasticity that allows them to extend apart, thus allowing the head of the implantable device to be disposed between the arms. The arms will then engage the through-holes 24 on the head of the implantable device. In this way the implanting tool can "grasp" the implantable device and allow the user (e.g., surgeon, physician, nurse, etc.) to insert and/or turn the implantable device at or near the implant site.

The implantation tool includes, but is not limited to, driver, wrench, spanner, screwdriver, or other turning tool, and the like that can engage the implantable device. The implantation tool may be used manually (e.g., turnable by hand) or by an automatic device (e.g., using a drill, power driver, etc.). The implantable device may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

Figure 5:
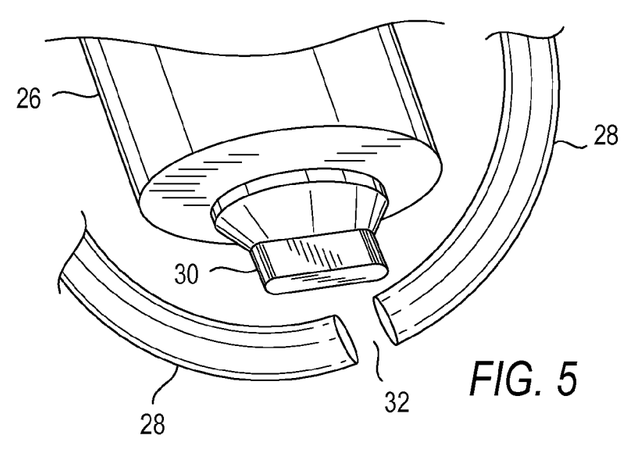
FIG. 5 illustrates an enlarged bottom view of an embodiment of the implanting tool suitable for engaging the head of the implantable device. The implanting tool having arms for engaging, among other things, the through-holes of the head of the implantable device.

FIG. 5 illustrates an enlarged bottom view of an embodiment of the implantation tool suitable for engaging the head of an implantable device. The implantation tool having a body 26 for the user to hold and arms 28 and edge 30 for engaging the through-holes and recess of the head of the implantable drug delivery device. In this illustrated embodiment, there is a gap 32 between the arms of sufficient elasticity that allows the arms to extend apart, allowing the head of the implantable device to be disposed between the arms.

Figure 6:
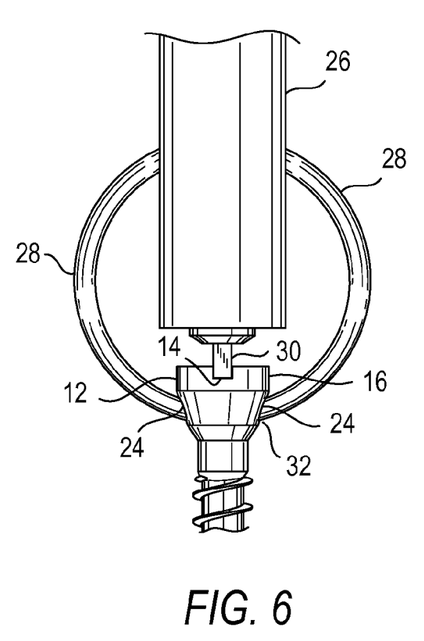
FIG. 6 illustrates an enlarged side view of an embodiment of the implanting tool engaging the head of the implantable device. The implanting tool's edge and arms engage the recess and the through-holes of the head of the implantable device.

FIG. 6 illustrates an enlarged side view of an embodiment of the implantation tool engaging the head 12 of the implantable device. The implanting tool's edge 30 and arms 28 engage the recess 14 and the through-holes 24 of the head of the implantable device as the gap 32 opens and the arms engage the through-holes. In this illustrated embodiment, the arms 28 engage the through-holes 24 and the user can hold the implantation device via body 26. The user can now turn the body of the implantation tool, which turns the head 12 of the implantable device causing the tip to be inserted into the site in such a manner so as to cause the outer surface of the shaft to engage the site. It will be understood by those of ordinary skill in the art that the implantation tool can snap into the holes, recess and/or projection of the device so that the user can lift the implantable device to one or more specific locations and turn the head of the implantable device causing the tip to be inserted into the site in such a manner so as to cause the outer surface of the shaft to engage the site.

In various embodiments, rotation of the implantation tool clockwise will cause the tip to engage the site and rotation of the implantation tool counterclockwise will cause the tip to disengage the site and allow the user to remove the device. In various embodiments, rotation of the implantation tool counterclockwise will cause the tip to engage the site and rotation of the implantation tool clockwise will cause the tip to disengage the site and allow the user to remove the device.

Figure 7:
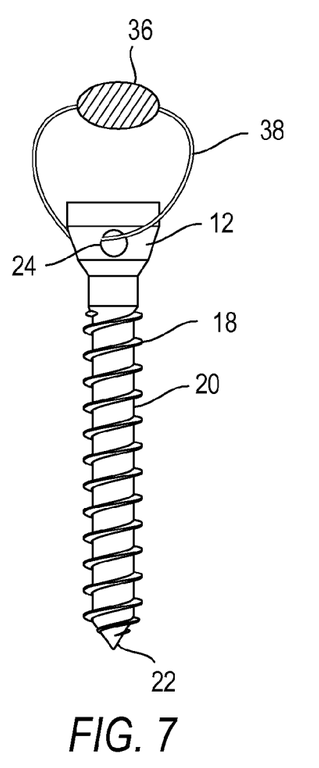
FIG. 7 illustrates an enlarged side view of an embodiment of the implantable device for anchoring a drug depot. In this illustrated embodiment, a drug depot is attached to the device.

FIG. 7 illustrates an enlarged side view of an embodiment of the implantable device for anchoring a drug depot 36. In this illustrated embodiment, a drug depot 36 is attached to the device and the implantable device comprises a screw head 12 having means for attaching the drug depot, the means comprising through-hole 24 that is capable of receiving the drug depot. For example, the drug depot may be attached to the implantable device by threading a suture or wire 38 having a drug depot disposed on it through the hole and tying it to the implantable device. Alternatively, the drug depot may be attached to the implantable device and then inserted at the target site. Thus, in various embodiments, the implantable device may be loaded with the drug depot before implantation. In other embodiments, the implantable device may be inserted first at the site then loaded with the drug depot.

The implantable device 10 of FIG. 7 comprises, among other things, a shaft 20 and a tip 22. The shaft 20 has a threaded outer surface 18 that engages the implant site in a manner that holds the device at the site beneath the skin. The tip 22 of the implantable device is opposite the head 12 and is capable of insertion into the site beneath the skin of the patient. The tip 22 of the device is designed to penetrate the site specific tissue and cause minimal physical and psychological trauma to the patient. The tip of the implant device may be designed for placement and location within or near a muscle, ligament, tendon, cartilage, bone, synovial joint, spinal disc space, spinal canal or the surrounding soft tissue.

The implantable device loaded with the depot is suitable for treatment of diseases or conditions requiring drug therapy. Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots with a quantity of pharmaceutical composition that can be deposited at the target site as needed for treatment of pain, inflammation or other disease or condition.

Figure 8:
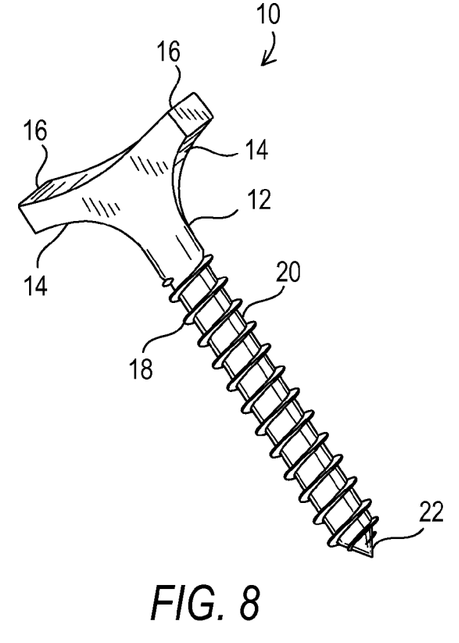
FIG. 8 illustrates an enlarged angled side view of an embodiment of the implantable device for anchoring a drug depot. In this illustrated embodiment, the head of the implantable device has two projections (shown as a cleat or wings) to attach the drug depot thereto.

FIG. 8 illustrates an enlarged angled side view of an embodiment of the implantable device 10 for anchoring a drug depot. In this illustrated embodiment, the implantable device 10 comprises a head 12 having at least one recess 14 and a plurality of projections 16 (shown as a cleat or wings) arranged to be engaged by an implanting tool (not shown) and means for attaching the drug depot to the implantable device. In the embodiment illustrated in FIG. 8, the means for attaching the drug depot comprises projections 16 that are capable of receiving the drug depot. For example, the drug depot may be attached to the implantable device by tying a suture or wire having a drug depot disposed on it around the projections to secure it (e.g., the suture can be tied into a basic knot, square knot, surgeon's or friction knot, etc.) to the implantable device.

The implantable device of FIG. 8 comprises, among other things, a shaft 20 and a tip 22. The shaft 20 has a threaded outer surface 18 that engages the implant site in a manner that holds the device at the site beneath the skin. The tip 22 of the implantable device is opposite the head 12 and is capable of insertion into the site beneath the skin of the patient. The tip 22 of the device is designed to penetrate the site specific tissue and cause minimal physical and psychological trauma to the patient. The tip of the implant device may be designed for placement and location within or near a muscle, ligament, tendon, cartilage, bone, synovial joint, spinal disc space, spinal canal or the surrounding soft tissue.

Figure 9:
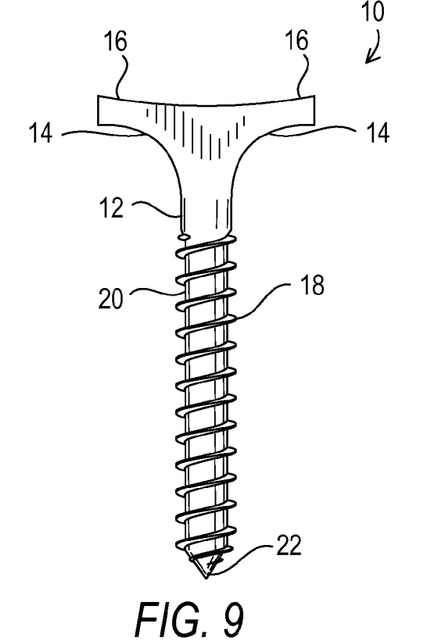
FIG. 9 illustrates an enlarged side view of an embodiment of the implantable device for anchoring a drug depot. In this illustrated embodiment, the head of the drug delivery device has two projections (shown as a cleat or wings) to attach the drug depot thereto.

FIG. 9 illustrates an enlarged side view of an embodiment of the implantable device for anchoring a drug depot. In this illustrated embodiment, the implantable device 10 comprises a head 12 having at least one recess 14 and a plurality of projections 16 (shown as a cleat or wings) arranged to be engaged by an implanting tool (not shown) and that functions as means for attaching the drug depot to the implantable device. In the embodiment illustrated in FIG. 9, the means for attaching the drug depot comprises projections 16 that are capable of receiving the drug depot. For example, the drug depot may be attached to the implantable device by tying a suture or wire having a drug depot disposed on it around the projections to secure it (e.g., tying a basic knot, square knot, surgeon's or friction knot, etc.) to the implantable device. The implantable device comprises, among other things, a shaft 20 and a tip 22. The shaft 20 has a threaded outer surface 18 that engages the implant site in a manner that holds the device at the site beneath the skin. The tip 22 of the implantable device is opposite the head 12 and is capable of insertion into the site beneath the skin of the patient. The tip 22 of the device is designed to penetrate the site specific tissue and cause minimal physical and psychological trauma to the patient.

Figure 10:
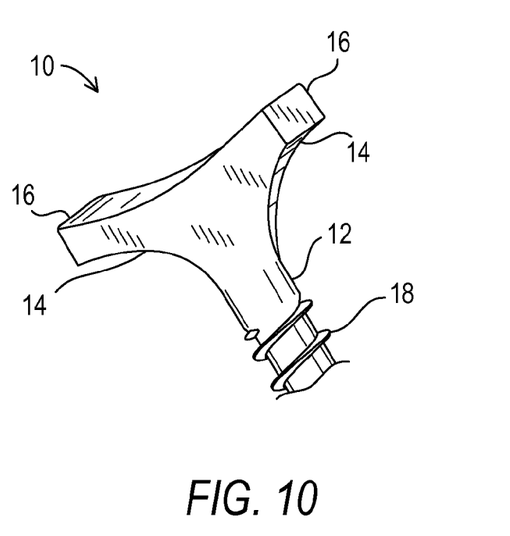
FIG. 10 illustrates an enlarged top view of an embodiment of the implantable device for anchoring a drug depot. In this illustrated embodiment, the head of the implantable device has two projections (shown as a cleat) to attach the drug depot.

FIG. 10 illustrates an enlarged side view of the upper portion of an embodiment of the implantable device for anchoring a drug depot having threads 18. In this illustrated embodiment, the implantable device 10 comprises a head 12 having at least one recess 14 and a plurality of projections 16 (shown as a cleat or wings) arranged to be engaged by an implanting tool (not shown) and that also function as means for attaching the drug depot to the implantable device. In the embodiment illustrated in FIG. 10, the means for attaching the drug depot comprises projections 16 that are capable of receiving the drug depot. For example, the drug depot may be attached to the implantable device by tying a suture or wire having a drug depot disposed on it around the projections to secure it (e.g., tying a basic knot, square knot, surgeon's or friction knot, etc.) to the implantable device. In this illustrated embodiment the head of the implantable device has two projections provided as a pair (shown as a cleat or wings).

Figure 11:
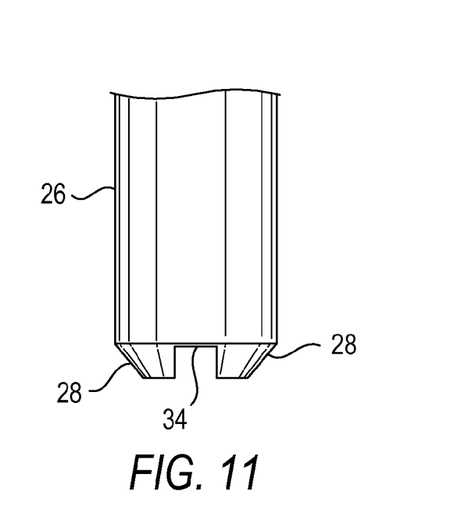
FIG. 11 illustrates an enlarged side view of an embodiment of a turning tool suitable for engaging the head of the implantable device. The turning tool having arms for engaging, among other things, the recess and projections of the head of the implantable device. In this illustrated embodiment, the turning tool is disengaged from the device.

FIG. 11 illustrates an enlarged side view of an embodiment of a turning tool suitable for engaging the head of the implantable device. The turning tool having a body 26 for the user to hold. Arms 28 and recess 34 for engaging the projection and recesses of the head of the implantable drug delivery device. In this illustrated embodiment, there is a recess 34 between the arms that allow the turning tool to be inserted in the recesses and projection of the head of the implantable device. In this way, the turning tool may snap fit into the implantable device and the device may be held by the user by holding the turning tool. In other embodiments, the turning tool engages the projection(s) or recess(es) of the head of the implantable device so that the device can be turned by the turning tool without the snap fit engagement. FIG. 11 illustrates the turning tool in the disengaged position (e.g., not engaging the implantable device).

Figure 12:
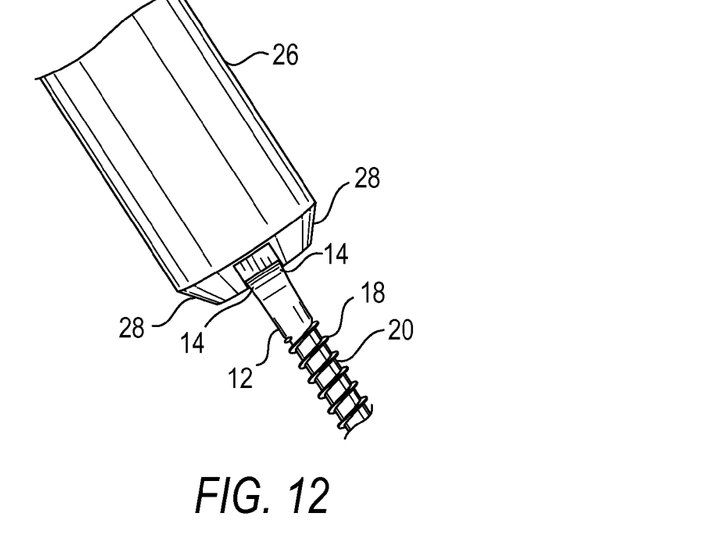
FIG. 12 illustrates an enlarged side view of an embodiment of the turning tool engaging the head of the implantable device. The turning tool's edge and arms engage the recess and projections of the head of the implantable device.

FIG. 12 illustrates an enlarged side view of an embodiment of the turning tool engaging the head of the implantable device. The turning tool's arms 28 engage the recess and projections of the head of the implantable device 12. The user can now turn the body 26 of the turning tool, which turns the head 12 of the implantable device causing the tip to be inserted into the site in such a manner so as to cause the outer threaded surface 18 of the shaft 20 to engage the site. It will be understood by those of ordinary skill in the art that the implantation tool can snap into the device and hold it through the recess and/or projection as well so that the user can turn the head of the implantable device causing the tip to be inserted into the site in such a manner so as to cause the outer surface of the shaft to engage the site. In various embodiments, rotation of the implantation tool clockwise will cause the tip to engage the site and rotation of the implantation tool counterclockwise will cause the tip to disengage the site and remove the device. In various embodiments, rotation of the implantation tool counterclockwise will cause the tip to engage the site and rotation of the implantation tool clockwise will cause the tip to disengage the site and allow the user to remove the device.

Figure 13:
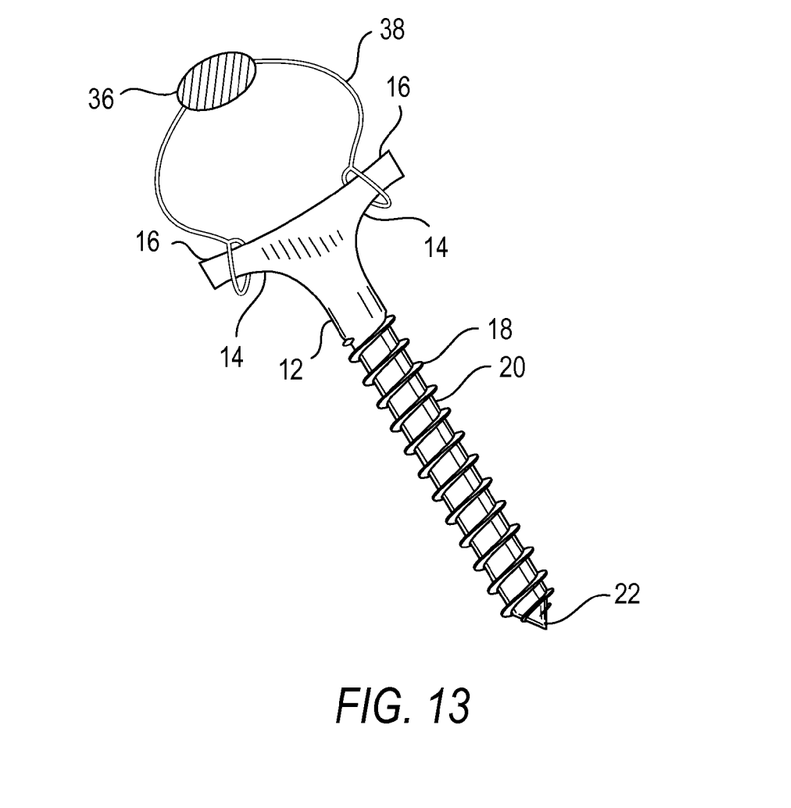
FIG. 13 illustrates an enlarged side view of an embodiment of the implantable device for anchoring a drug depot. In this illustrated embodiment a drug depot is attached to the device.

FIG. 13 illustrates an enlarged side view of an embodiment of the implantable device for anchoring a drug depot. In this illustrated embodiment, the implantable device comprises a screw head 12 having means for attaching the drug depot 36, in this case, a plurality of projections 16 (shown as a cleat or wings) and recesses 14 arranged to be engaged by an implanting tool (not shown) and that also function as means for attaching the drug depot to the implantable device. For example, the drug depot 36 may be attached to the implantable device by tying a suture or wire 38 having a drug depot 36 disposed on it around the projections 16 to secure it by for example, making a knot (e.g., basic knot, square knot, surgeon's or friction knot, etc.) to hold the drug depot 36 in place on the implantable device. In this illustrated embodiment the head of the implantable device has two projections (shown as a cleat or wings). Alternatively, the drug depot may be first attached to the implantable device and then subsequently inserted at the target site. Thus, in various embodiments, the implantable device may be loaded with the drug depot before implantation. In other embodiments, the implantable device may be inserted at the site then loaded with the drug depot.

The implantable device of FIG. 13 comprises, among other things, a shaft 20 and a tip 22. The shaft 20 has a threaded outer surface 18 that engages the implant site in a manner that holds the device at the site beneath the skin. The tip 22 of the implantable device is opposite the head 12 and is capable of insertion into the site beneath the skin of the patient. The tip 22 of the device is designed to penetrate the site specific tissue and cause minimal physical and psychological trauma to the patient.

Figure 14:
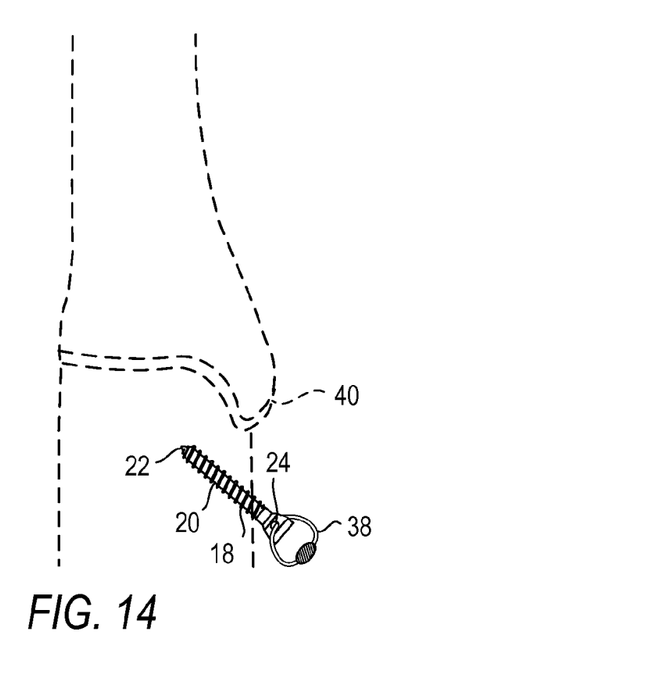
FIG. 14 illustrates an enlarged side view of an embodiment of the implantable device implanted at a target site, in this case, near the synovial joint. The implantable device has a drug depot attached to the through-holes of the head of the implantable device. The drug depot is adjacent to the synovial joint.

FIG. 14 illustrates an enlarged side view of an embodiment of the implantable device implanted at a target site, in this case, near the synovial joint 40. Although the synovial joint is shown, the device can be used to deliver a drug depot to any site beneath the skin, including, but not limited to, at least one muscle, ligament, tendon, cartilage, spinal disc, or spinal canal. The implantable device has a drug depot 36 attached to the through-holes 24 of the head of the implantable device. The implantable device may be implanted at the target site and the drug depot 36 will be at or near the target site, in this case, adjacent to the synovial joint 40. In this illustrated embodiment, the implantable device comprises a screw head 12 having means for attaching the drug depot comprising through-hole 24 that is capable of receiving the drug depot 36. For example, the drug depot may be attached to the implantable device by threading a suture or wire 38 having a drug depot disposed on it through the hole and tying it to the implantable device thereto. Alternatively, the drug depot may be attached to the implantable device and then inserted at the target site. Thus, in various embodiments, the implantable device may be loaded with the drug depot before implantation. In other embodiments, the implantable device may be inserted at the site then loaded with the drug depot.

The suture 38 may be made from a biodegradable or non-biodegradable material. If made from a biodegradable material, it may be desirable to select a material for the suture that degrades significantly slower than the implantable device. By tying the suture 38 onto the device, it is possible to securely retain the drug depot 36 at or adjacent to a targeted tissue site, and hence prevent translational movement of the drug depot within or from the targeted tissue site.

Examples of suitable biodegradable material for the suture include, but is not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof.

Figure 15:
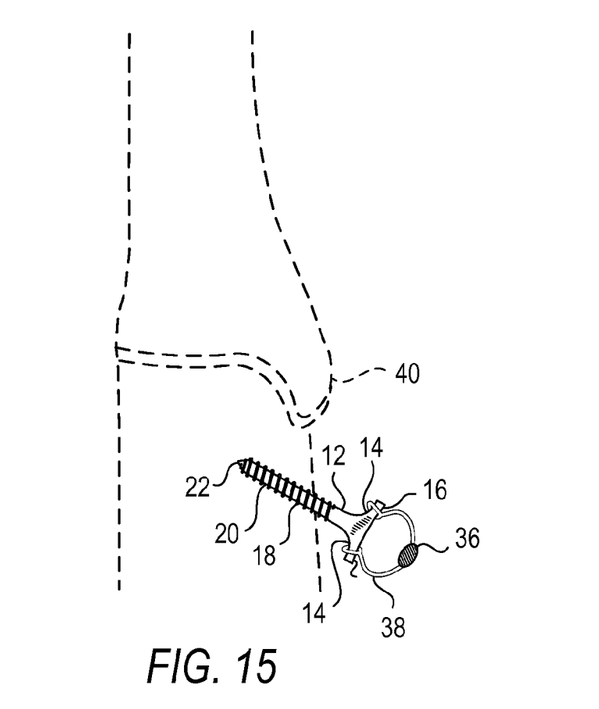
FIG. 15 illustrates an enlarged side view of an embodiment of the implantable device implanted at a target site, in this case, near the synovial joint. The implantable device has a drug depot attached to the projections of the head of the implantable device. The drug depot is adjacent to the synovial joint.

FIG. 15 illustrates an enlarged side view of an embodiment of the implantable device implanted at a target site, in this case, near the synovial joint 40. The implantable device has a drug depot 36 attached to the projections 16 of the head 12 of the implantable device. The drug depot is adjacent to the synovial joint 40. In this illustrated embodiment, the implantable device comprises a screw head 12 having means for attaching the drug depot 36, in this case, a plurality of projections 16 (shown as a cleat or wings) and recesses 14 arranged to be engaged by an implanting tool (not shown) and that also function as means for attaching the drug depot to the implantable device. For example, the drug depot 36 may be attached to the implantable device by tying a suture or wire 38 having a drug depot 36 disposed on it around the projections 16 to secure it by for example, making a knot (e.g., basic knot, square knot, surgeon's or friction knot, etc.) to hold the drug depot 36 in place on the implantable device. In this illustrated embodiment, the head of the implantable device has a plurality of projections (shown as a cleat or wings). Alternatively, the drug depot may be attached to the implantable device and then inserted at the target site. Thus, in various embodiments, the implantable device may be loaded with the drug depot before implantation. In other embodiments, the implantable device may be inserted at the site then loaded with the drug depot.

The implantable device of FIG. 15 comprises, among other thing, a shaft 20 and a tip 22. The shaft 20 has a threaded outer surface 18 that engages the implant site in a manner that holds the device at the site beneath the skin. In this way, the drug depot is stabilized at the site and migration of the drug depot is reduced. The tip 22 of the implantable device is opposite the head 12 and is capable of insertion into the site beneath the skin of the patient. The tip 22 of the device is designed to penetrate the site specific tissue and cause minimal physical and psychological trauma to the patient. In various embodiments, the contemplated placement of the implantable device at the site will cause minimal or no damage to the bone, cartilage surface or tissue.

In various embodiments, the device may be positioned in an intra-articular site of a synovial joint where there is no interfacing articular cartilage. It may be located, for example, within the inside of the knee capsule that is non-load-bearing and removed from the articulation surface of the synovial joint. The device may be attached within the synovial joint, allowing for continuous exposure to synovial fluid flow and resulting release of the drug from the drug depot, without damaging the articular surface that is in apposition during range of motion of the given joint. Because the drug depot is anchored to the device, the risk of unwanted migration in the joint is reduced. Accordingly, target directed treatment at the site may be accomplished and the desired therapeutic concentration of the drug to be achieved at the site and the duration of drug concentration can be maintained.

Radiographic markers can be included on the implantable device and/or drug depot to permit the user to accurately position the depot into the desired site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads. For example, the radiographic marker can be ring-shaped or dispersed as small pellets throughout the implantable device.

In various embodiments, the implantable device or drug depot may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the implantable device or drug depot relative to the absence of the material or topography.

Drug Depot

In various embodiments, the device comprises a drug depot attached thereto. A drug depot comprises a physical structure to facilitate implantation and retention in a desired site (e.g., a synovial joint, a disc space, a spinal canal, a tissue of the patient, etc.) or adjacent to the desired site. The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, gels, coating, matrices, wafers, pills, cartridges, pellets or other pharmaceutical delivery compositions. A depot may comprise a biopolymer that is either biodegradable or non-degradable. A depot may comprise a biopolymer that may provide for immediate release or sustained release or controlled release. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof.

The drug depot may be any shape, for example, bullet shaped, spherical, substantially spherical, flaked, rod shaped, square, oval, etc. The drug depot comprises a body that is made from a biodegradable material. In alternative embodiments, the body may be made from a non-biodegradable material. A non-biodegradable body could be a porous hollow chamber filled with the therapeutic agent alone or incorporated into a degradable polymer. It may be desirable to make the body non-degradable to be able to retrieve it after it has released or exhausted its contents. Or the non-biodegradable body could be a small pump that pushes the contents out pores, port(s), or a cannula. The body of the drug depot may be solid and a therapeutic agent may be dispersed throughout the material that forms the body. The dispersal of the therapeutic agent may be even throughout the body or in various parts of the body in layers (e.g., one third, two thirds, three fourths, etc.).

As the biodegradable material of the body degrades within the tissue, the therapeutic agent is released. Suitable sustained release materials may be used in the drug depot to carry the one or more therapeutic agents and control the release of the therapeutic agent(s). For example, microspheres may be used to encapsulate the therapeutic agent; the therapeutic agent-containing microspheres are then dispersed through the body of the drug depot.

In various embodiments, the drug depots are contemplated for use in the intervertebral disc and joint capsules, which includes bead-shaped depots strung together along a suture or wire. In this embodiment, the beads may be a drug-loaded biodegradable polymer, and the suture or wire may be either degradable or non-degradable material.

The drug depot can be designed for gradient variations in biodegradability to hold the depot in place while the secondary material releases its contents. The drug depot may have a width from about 1 mm to about 6 mm and a length from about 5 mm to about 20 mm. Selection of suitable lengths and widths for the drug depot will depend upon the targeted implant site, dosage required and is well within the abilities of those having ordinary skill in the art.

In various embodiments, procedures for making the drug depot include, but are not limited to, extrusion-spheroidization, for spherical depots where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate the resultant drug depot size. The extrudate is fed onto a rotating disk, which may be smooth or may contain a grid (waffled, grooved, etc.) and the extrudate breaks into small cylinders, which in time are rounded into spherically shaped solids. Subsequently, the drug depots are dried to the desired residual moisture content, typically in a fluid bed dryer. Any oversized or undersized product is removed by sieving, and the resulting drug depots have a narrow size distribution.

In various embodiments, the API is layered on the solid body of the drug depot by solution or suspension layering or powder layering techniques. In solution or suspension layering, an API and any inactive ingredients (excipients, binders, etc.) are suspended or dissolved in water or an organic solvent. The resulting liquid is sprayed onto the outside of a body, which may include, for example, non-pareil sugar seed (sugar sphere), microcrystalline cellulose depots and the like, to make the depot having the desired potency. Solution or suspension layering may be conducted using a wide variety of process techniques, for example, by fluidized bed, Wurster bottom spray techniques, or the like. When the desired potency has been achieved, the depots are dried to the desired residual moisture content. Any oversized or undersized product may be removed by sieving, and the resulting depots are narrow in size distribution.

Powder layering may also be used to make the drug depot. Powder layering involves the application of a dry powder to the body material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the body material while applying the dry powder until the desired potency is achieved. When the desired potency has been achieved, the drug depots may be seal coated to improve their strength, and are then dried to the desired moisture content. Any oversized or undersized product is removed by sieving, and the resulting drug depots are narrow in size distribution.

In one embodiment, the drug depot is made using a body of biodegradable material, such as, for example, polyglactin, polylactone, polylactide, etc. The body is then coated with a thin layer of the API, such as an anti-inflammatory agent, analgesic agent, etc. by solution, suspension, or powdered layering until the desired potency is achieved.

In various embodiments, the drug depot can be different sizes, for example, from about 1 mm to 5 mm and have a diameter of from about 0.01 to about 2 mm. The layer or layers will each have a layer thickness of from about 0.005 to 1.0 mm, such as, for example, from 0.05 to 0.75 mm.

The implantable device and/or drug depot may be disposable and sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In various embodiments, a kit is provided which may include additional parts along with the implantable device combined together to be used to implant the drug depot. The kit may include the drug depot device in a first compartment. A second compartment may include the drug depot, and the implantation tool, turning tool, and any other instruments needed for the implant. A third compartment may include gloves, drapes, wound dressings and other procedural supplies for maintaining sterility during the implanting process, as well as an instruction booklet. A fourth compartment may include cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method is provided for delivering a drug depot adjacent to a site beneath the skin of a patient, the method comprising: implanting a device comprising a head, a shaft and a tip, the head having a recess and/or at least one projection capable of being engaged by a turning tool and means for attaching the drug depot thereto, the shaft having a threaded outer surface that engages the site in a manner that holds the device at the site beneath the skin, and the tip being located on the shaft opposite the head and being capable of insertion to the site beneath the skin of the patient; engaging the recess and/or the projection of the head with the turning tool and turning the head causing the tip to be inserted into the site in such a manner so as to cause the outer surface of the shaft to engage the site; and attaching the drug depot to the recess and/or the projection of the head of the device, thereby anchoring the drug depot adjacent to the site beneath the skin of the patient.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

In various embodiments, the drug depot is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

In various embodiments, once the device is anchored at the implant site and the drug is released from the drug depot over a period of time (e.g., days, months, years, etc.) and exhausted, the user (e.g., surgeon, physician, nurse, etc.) may remove the exhausted drug depot from the device without removing the implantable device itself.

For example, the user can clip or cut the suture line holding the drug depot and replace it with another new drug depot. In this way, accurate and precise implantation of the replacement drug depot with minimal physical and psychological trauma to the patient result. Now successful treatment plans can be continued by merely replacing exhausted drug depots with new drug depots position at one or more treatment sites. In various embodiments, the drug depot is removed without removing the device.

Radiographic markers can be included on the implantable device and/or drug depot to permit the user to accurately position the depot into the site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. When a subsequent image is taken of the treatment site, the user now can look for the degraded or exhausted drug depot and remove it and replace it with a new drug depot having fresh drug at the same or different dosage by, for example, threading a new suture or wire having the drug depot disposed on it through the hole and tying it to the device or tying it to al least one or more projections of the implantable device.

The dosage administered, to an individual as single or multiple doses will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable device for anchoring a drug depot adjacent to a site beneath the skin of a patient, the device comprising: a head, a shaft and a tip, the head having a recess and/or at least one projection arranged to be engaged by an implantation tool, the shaft having an outer surface that engages the site in a manner that holds the device at the site beneath the skin, the head fixed to the shaft and being incapable of movement relative to the shaft, the head or shaft having means for attaching the drug depot thereto, the tip disposed on the shaft opposite the head and capable of insertion into the site beneath the skin of the patient, and the drug depot being a solid biodegradable drug depot attached to the implantable device above the head, the drug depot configured to release a therapeutic agent as the drug depot degrades.

2. An implantable device according to claim 1, wherein the outer surface comprises threading and the means for attaching the drug depot comprises one or more through-holes disposed radially through the head of the device below the recess and/or projection.

3. An implantable device according to claim 1, wherein the implantation tool is a driver having a body, two arms and an edge, the body for a user to hold and the arms for engaging the means for attaching the drug depot, the means comprising at least two through-holes in the head and the edge for engaging the recess of the head, wherein rotating the implantation tool in a clockwise direction causes the tip of the device to be held at the site beneath the skin.

4. An implantable device according to claim 1, wherein the head has two surfaces, each surface having a through-hole thereon and each through-hole connected by a channel for receiving a suture line attached to the drug depot.

5. An implantable device according to claim 2, wherein the drug depot is attached to the through-holes of the implantable device.

6. An implantable device according to claim 1, wherein the means for attaching the drug depot comprises one or more through-holes disposed in the head of the device and the drug depot is attached to the one or more through-holes by a suture line or wire.

7. An implantable device according to claim 5, wherein the drug depot contains markings that indicate location at or near the site beneath the skin.

8. An implantable device according to claim 1, wherein the drug depot comprises an anti-inflammatory agent, analgesic agent, or osteoinductive growth factor or a combination thereof.

9. An implantable device according to claim 1, wherein the site is at least one muscle, ligament, tendon, cartilage, bone, synovial joint, spinal disc, or spinal canal.

10. An implantable device for anchoring a drug depot to a site beneath the skin of a patient, the device comprising: a head, a shaft and a tip, the head having a recess and/or a projection arranged to be engaged by a turning tool and for attaching the drug depot thereto, the head fixed to the shaft and being incapable of movement relative to the shaft, the shaft having a threaded outer surface that engages the site in a manner that holds the device at the site beneath the skin, the tip being located on the shaft opposite the head and capable of insertion into the site beneath the skin of the patient, and the drug depot being a solid biodegradable drug depot attached to the implantable device above the head, wherein the drug depot is configured to release a therapeutic agent as the drug depot degrades.

11. An implantable device according to claim 10, wherein the device is a screw and the drug depot is attached to a plurality of projections disposed on the head and the plurality of projections and/or the recess are arranged to be engaged by the turning tool.

12. An implantable device according to claim 10, wherein the turning tool is a driver having a body, two arms and a recess, the body for a user to hold and the arms and recess for engaging the head, wherein rotating the turning tool in a clockwise direction causes the tip of the device to be held at the site beneath the skin.

13. An implantable device according to claim 10, wherein at least two projections are disposed on the head, each projection capable of receiving the drug depot or a suture line or wire attached to the drug depot.

14. An implantable device according to claim 13, wherein the site is at least one muscle, ligament, tendon, cartilage, bone, synovial joint, spinal disc, or spinal canal.

15. An implantable device according to claim 13, wherein the drug depot is attached to the at least two projections of the head by a suture line, or wire.

16. An implantable device according to claim 15, wherein at least one of (i) the device comprises non-biodegradable material or (ii) the drug depot contains markings that indicate location at or near the site beneath the skin.

* * * * *